(12) United States Patent
Seo et al.

(10) Patent No.: US 9,899,115 B1
(45) Date of Patent: Feb. 20, 2018

(54) TERAHERTZ TRAPPING DEVICE

(71) Applicant: Korea Institute of Science and Technology, Seoul (KR)

(72) Inventors: Min Ah Seo, Seoul (KR); Dong Kyu Lee, Seoul (KR); Geun Chang Choi, Seoul (KR); Chul Ki Kim, Seoul (KR); Jae Hun Kim, Seoul (KR); Taik Jin Lee, Seoul (KR); Young Min Jhon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/428,692

(22) Filed: Feb. 9, 2017

(30) Foreign Application Priority Data

Nov. 24, 2016 (KR) .................. 10-2016-0157169

(51) Int. Cl.
*G21K 5/04* (2006.01)
*G21K 5/08* (2006.01)

(52) U.S. Cl.
CPC ................... *G21K 5/04* (2013.01); *G21K 5/08* (2013.01)

(58) Field of Classification Search
CPC ........ G01N 27/44791; G01N 27/44713; B03C 5/005; B03C 5/02; B01L 3/502715; B01L 3/502761; B01L 2300/0864; B01L 2200/0647; B01L 2300/0645; B01L 2300/0816; B01L 2300/0877; G21K 5/04; G21K 5/08
USPC ............................................. 250/251, 453.11
See application file for complete search history.

(56) References Cited

U.S. PATENT DOCUMENTS

2015/0330951 A1* 11/2015 Gordon .................. G01N 15/10
　　　　　　　　　　　　　　　　　　　　　　　73/643
2016/0231274 A1* 8/2016 Tirapu
　　　　　　　　　　　　Azpiroz ........... G01N 27/44791

FOREIGN PATENT DOCUMENTS

KR　　10-0849928 B1　　8/2008
KR　　10-2012-0093629 A　　8/2012

* cited by examiner

*Primary Examiner* — Michael Maskell
(74) *Attorney, Agent, or Firm* — NSIP Law (57) ABSTRACT

Disclosed is a terahertz trapping device including a substrate, and a film disposed on the substrate, wherein the film has a slot in a particular shape patterned to be engraved or a structure in a particular shape patterned by embossing the film to control motion of a particle using terahertz electromagnetic waves.

11 Claims, 9 Drawing Sheets
(9 of 9 Drawing Sheet(s) Filed in Color)

TERAHERTZ TRAPPING DEVICE

CROSS-REFERENCE TO RELATED APPLICATION

This application claims priority to and the benefit of Korean Patent Application No. 10-2016-0157169, filed on Nov. 24, 2016, the disclosure of which is incorporated herein by reference in its entirety.

BACKGROUND

1. Field of the Invention

The present invention relates to a trapping technology, and more particularly, to a terahertz trapping device using terahertz electromagnetic waves and a terahertz metamaterial specific to the terahertz electromagnetic waves.

2. Discussion of Related Art

Terahertz electromagnetic waves correspond to electromagnetic waves in a range of 0.1 to 10 THz relative to a frequency (1 THz) corresponding to 10 to the power of 12 vibrations per second. Terahertz electromagnetic waves in such a band are harmless to human body when it does not exceed a threshold value due to nonionizing property and have properties of penetrating various materials excluding metals. In addition, owing to such penetration property, terahertz electromagnetic waves can easily penetrate a weapon or the like, which is made of a metal and hidden in clothes, and have been developed as a millimeter wave scanner to substitute for x-ray to be used at airports in the United States. In addition, terahertz electromagnetic waves are actively utilized in spectrometers in research and development because there are numerous materials that strongly absorb at specific frequencies. Particularly, terahertz electromagnetic waves can be used to easily distinguish narcotics and toxic substances that cannot be easily distinguished by human eyes.

However, in spite of such features of the terahertz electromagnetic frequency band, most of conventional trapping technologies use visible or infrared (IR) light, and thus there are difficulties in performing non-ionized and nondestructive inspection of a bio-material.

Korean Patent Registration No. 10-0849928 entitled "3 Dimensional Optoelectronic Tweezers System and the Microfluidic Manipulation Method thereof" discloses a three dimensional optoelectronic tweezers system technology, on the basis of an optical tweezers system, for solid particles in a microfluid flowing between a pair of photoconductive layers, and Korean Patent Registration No. 10-2012-0093629 entitled "Optical Tweezers System and Method of Trapping Micro-object using the same" discloses a technology of using an optical tweezers system in which a laser beam and an optical section which forms a trap are changed depending on the number and shape of micro-objects, however, difficulties of the conventional technologies for inspecting a bio-material have still not been resolved.

RELATED ART DOCUMENT

Patent Document (Patent Document 1) Korean Patent Registration No. 10-0849928
(Patent Document 2) Korean Patent Laid-Open Publication No. 10-2012-0093629

SUMMARY OF THE INVENTION

The present invention is directed to providing a terahertz trapping device capable of capturing micro-objects using electromagnetic waves of a new wavelength, that is, terahertz electromagnetic waves, unlike capturing micro-objects using a conventional laser.

Another objective of the present invention is directed to providing a terahertz trapping device capable of strongly amplifying and focusing terahertz electromagnetic waves (0.1 to 2.5 THz) using a terahertz metamaterial, thereby being capable of inducing small beads or particles to be trapped at a particular position and controlling the motion of the small beads or particles.

According to an aspect of the present invention, there is provided a terahertz trapping device including a substrate, and a film disposed on the substrate, wherein the film includes a slot in a particular shape patterned to be engraved or a structure in a particular shape patterned by embossing the film to control motion of a particle using terahertz electromagnetic waves.

The particle on the film may be induced to be trapped in the patterned slot in a particular shape or the patterned structure in a particular shape by the terahertz electromagnetic waves.

The terahertz electromagnetic waves may be in a range of 0.1 to 2.5 THz and may be amplified and focused due to the film in which the slot is patterned to be engraved in a particular shape or the structure is patterned in a particular shape by embossing the film.

The slot or the structure may be formed according to a natural absorption frequency of the particle.

The slot or the structure may correspond to a rectangular shape and a number of the slots or the structures may be arranged.

The slot or the structure may include a bowtie shape formed at the center of the rectangular shape.

The slots or the structures may be arranged to be spaced by a distance of 0 to 1 mm in width and longitudinal directions on the substrate.

A length of the slot or the structure may be in a range of 10 μm to 1 mm.

The substrate may be formed of quartz, silicon, sapphire, or glass which is not influenced by electromagnetic waves.

The film may be formed of gold, silver, copper, or aluminum.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, advantages, features of the present invention and methods of accomplishing them will be made apparent with reference to the accompanying drawings and some embodiments to be described below. The present invention may, however, be embodied in different forms and should not be construed as being limited to the embodiments set forth herein. Rather, the embodiments are provided so that this disclosure is thorough and complete and fully conveys the inventive concept to those skilled in the art, and the present invention should only be defined by the appended claims. The same reference numerals indicate the same components throughout the specification. As used herein, the term "and/or" includes any and all combinations of one or more of the associated listed items.

Although the terms "first," "second," etc. may be used herein to describe various elements, components, and/or sections, these elements, components, and/or sections should not be limited by these terms. These terms are only used to distinguish one element, component, and/or section from another element, component, and/or section. Therefore, a first element, a first component, and/or a first section used below could be termed a second element, a second component, and/or a second section without departing from the technical concept and sprit of the present invention.

Meanwhile, the terminology used herein is for the purpose of describing particular embodiments only and is not intended to limit the present invention. As used herein, the singular forms "a," "an," and "the" are intended to include the plural forms as well unless clearly indicated otherwise by context. It should be further understood that the terms "comprises" and "comprising" specify the presence of stated features, integers, steps, operations, elements, and/or components when used herein, but do not preclude the presence or addition of one or more other features, integers, steps, operations, elements, components, and/or groups thereof.

Unless otherwise defined, all terms including technical and scientific terms used herein will be used with the same meaning as commonly understood by one of ordinary skill in the art to which this present invention belongs. It should be further understood that terms such as those defined in commonly used dictionaries are not to be interpreted in an idealized or overly formal sense unless expressly so defined herein.

In the following description, detailed descriptions of well-known functions or configurations will be omitted where they may unnecessarily obscure the subject matters of the invention. In addition, terms described below are defined considering functions of the present invention, but the terms may be changed by intention or practice of users and operators. Thus, definitions of these terms should be made on the basis of the content throughout the specification.

Figure 1:
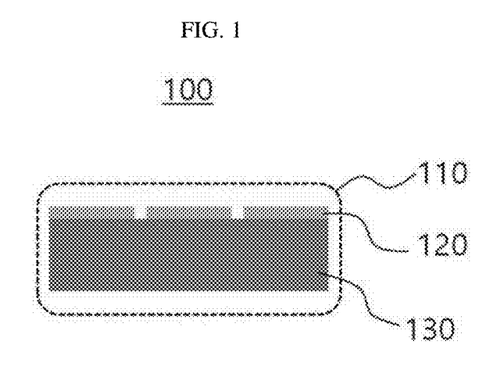
FIG. 1 is a cross-sectional view of a terahertz trapping device according to one embodiment of the present invention.

FIG. 1 is a cross-sectional view of a terahertz trapping device according to one embodiment of the present invention.

Referring to FIG. 1, a terahertz trapping device 100 includes a terahertz metamaterial 110, and the terahertz metamaterial 110 is configured with a film 120 and a substrate 130.

The terahertz metamaterial 110 refers to a structure itself in which the film 120 with slots left in an engraved shape is mounted on the substrate 130.

The film 120 is patterned to be engraved so as to have slots in a particular shape and disposed on the substrate 130. It is preferable that the film 120 be formed of gold, silver, copper, or aluminum.

The substrate 130 may be formed of quartz, silicon, sapphire, or glass which is not influenced by electromagnetic waves.

Figure 2:
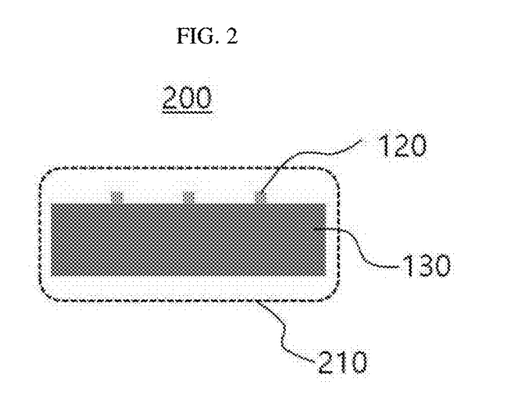
FIG. 2 is a cross-sectional view of a terahertz trapping device according to another embodiment of the present invention.

FIG. 2 is a cross-sectional view of a terahertz trapping device according to another embodiment of the present invention.

Referring to FIG. 2, a terahertz trapping device 200 includes a terahertz metamaterial 210, and the terahertz metamaterial 210 is configured with a film 120 and a substrate 130.

The terahertz metamaterial 210 refers to a structure itself in which the film 120 with only embossing structures is mounted on the substrate 130.

The film 120 may be patterned in a particular structure by embossing the film, and it is preferable that the film 120 be formed of gold, silver, copper, or aluminum.

The substrate 130 may be formed of quartz, silicon, sapphire, or glass which is not influenced by electromagnetic waves.

Hereinafter, the terahertz trapping devices 100 and 200 will be described in detail with reference to FIGS. 1 and 2.

A terahertz electromagnetic wave used in the embodiments of the present invention is an electromagnetic wave in a low energy band which is incapable of ionizing a target object, and a wavelength thereof is several tens to several thousand times longer compared to a wavelength of a laser light source used in a conventional optical tweezers technology. When the terahertz metamaterials 110 and 210 specially designed are applied to the terahertz electromagnetic wave to implement a method for capturing microobjects, it has various application potentials that may be applied to fields to which it is difficult to attempt applying conventional optical tweezers technologies. In addition, an optical trap is a method of trapping particles or forcing particles to move using force generated when laser light is focused on dielectric particles through an objective lens, wherein, since the force working thereon is due to refraction of light passing through the particles, stronger force may work thereon when a large lens with a greater focusing capability is used, and, as in the case of the optical trap, for a terahertz electromagnetic wave trap, a terahertz electromagnetic wave needs to be focused to a particle size to trap the particles.

The embodiments of the present invention relate to the terahertz trapping devices 100 and 200, which may strongly amplify and focus electromagnetic waves, using the terahertz metamaterials 110 and 210 together with the terahertz electromagnetic waves, which may focus the electromagnetic waves to a very small area compared to the wavelength of the electromagnetic waves beyond the limit imposed by the wavelength, which may have an effect of increased penetration (or reflection) efficiency of over 100 to 10,000 times compared to a conventional simple type of electromagnetic waves oscillation device, and the efficiency thereof may be determined by a design of the terahertz metamaterials 110 and 210. Among various types of terahertz metamaterial designs, when tetragonal-shaped holes are repeatedly arranged, resonance characteristics of the interacting terahertz electromagnetic waves become different according to a width and length of the holes.

Meanwhile, since there is a natural absorption vibration mode of most material in a terahertz electromagnetic wave band, design of the terahertz metamaterials 110 and 210 may be configured to meet the natural absorption frequency of the particular material. When terahertz electromagnetic waves amplified and focused to meet characteristics of the designed terahertz metamaterials 110 and 210 are used, a particular material may be detected at low concentration with high sensitivity. Particularly, since absorption vibration modes inherent to a material are diverse, high selectivity may be given according to the characteristics of the terahertz metamaterials 110 and 210 used.

When the terahertz metamaterials 110 and 210 having a structure in which the film 120 with slots left in an engraved shape or only embossing structures left is mounted on the substrate 130 according to the embodiments of the present invention are used, terahertz electromagnetic waves in a range of 0.1 to 2.5 THz may strongly be amplified and focused, and thereby small beads or particles may be induced to be trapped in a particular position. In addition, when such terahertz metamaterials 110 and 210 are used, a terahertz tweezers technology using motion control of small beads or particles may be implemented and is applicable to a conventional field in which an optical tweezers technology is being applied and new fields in which characteristics of terahertz electromagnetic waves may be utilized. Particularly, the embodiments of the present invention may be applied as a technology for realizing a new molecular sensing based on the fact that diverse materials have strong absorption and spectroscopic characteristics in the terahertz frequency band.

The terahertz metamaterials 110 and 210 according to the embodiments of the present invention may be configured so that the film 120 having an embossing pattern or engraved-pattern in a rectangular shape or a rectangular shape whose center is formed in a bowtie shape is disposed on the substrate 130, and hereinafter, the following descriptions will be based on a slot in a rectangular shape or a rectangular shape whose center is formed in a bowtie shape formed on the film 120. However, the following descriptions on the slot may also be equally applicable, when the film 120 is disposed on the substrate 130 as a structure in a rectangular shape or a rectangular shape whose center is formed in a bowtie shape.

Figure 3:
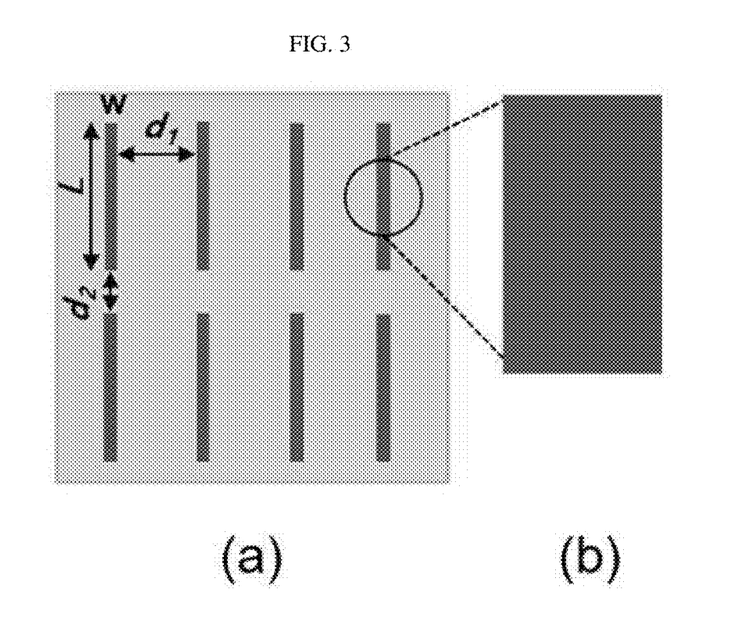
FIG. 3 is a view for describing a slot in a rectangular shape.
Figure 4:
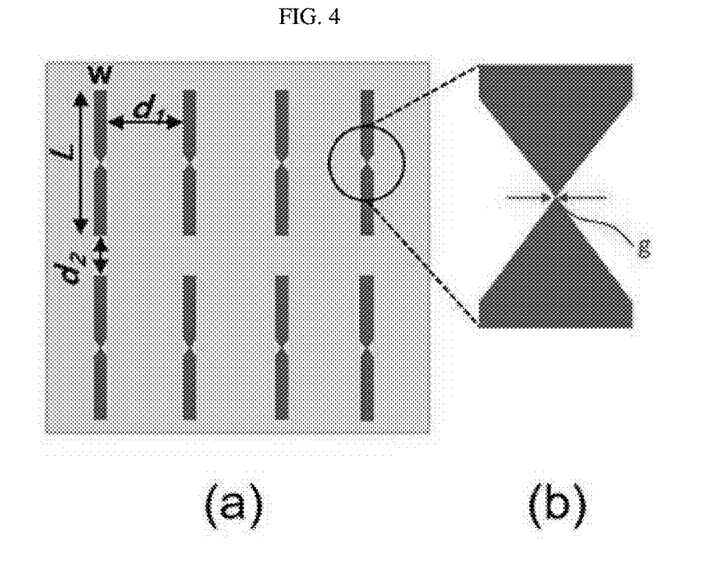
FIG. 4 is a view for describing a slot in a rectangular shape in which a bowtie shape is formed.

FIG. 3 is a view for describing a slot in a rectangular shape, and FIG. 4 is a view for describing a slot in a rectangular shape in which a bowtie shape is formed.

For trapping particles using terahertz electromagnetic waves, since terahertz electromagnetic waves need to be focused to a size as small as a particle size which is several thousand times smaller than a wavelength of terahertz electromagnetic waves, the terahertz metamaterials 110 and 210 in a slot (a hole) shape (engraved-patterning) or a structural shape (embossing patterning) having a length of several hundred micrometers and a width of nanometer size are used so that resonance can occur in the wavelength of terahertz electromagnetic waves. Hereinafter, the following descriptions will be based on a slot shape, but a structural shape may also be equally applied thereto.

Referring to FIGS. 3 and 4, the slots may correspond to a rectangular shape as illustrated in (a) of FIG. 3 or a rectangular shape whose center is formed in a bowtie shape as illustrated in (a) of FIG. 4. Both types of the slots in a rectangular shape and a rectangular shape whose center is formed in a bowtie shape may be patterned to be engraved on the film 120, as illustrated in FIG. 1.

It is preferable that a plurality of slots in a rectangular shape or a rectangular shape whose center is formed in a bowtie shape may be arranged to be spaced by a distance of 0 to 1 mm both in width $d_1$ and length $d_2$. When slots are patterned to be engraved, slots (holes) may be formed at the film 120 that is mounted on the substrate 130, and when the film 120 is patterned in a structural shape by embossing the film 120, the film 120 having the structures may be disposed on the substrate 130. In addition, the individual slots in a rectangular shape or a rectangular shape whose center is formed in a bowtie shape may have a width W corresponding to a range of several hundred nanometers to several micrometers and a length L corresponding to a range of 10 micrometers to 1 millimeter.

Referring to a portion indicated by red arrows of (b) of FIG. 4, it is preferable that a node width g at the center of the bowtie shape of the slot in the rectangular shape in which the bowtie shape is formed may be in a range of zero to several tens micrometers, wherein when "g=0", it corresponds to a shape in which both divided halves of the slit are attached without a gap because the node width is not formed at the center of the bowtie shape, and thus a transmission spectrum may exhibit an effect of pinch harmonics.

Figure 5:
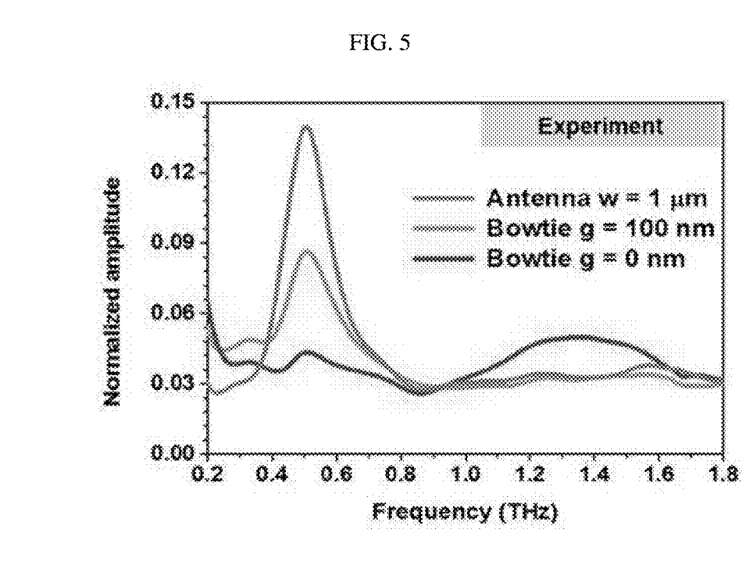
FIG. 5 is a view illustrating transmittance depending on slot shape.

FIG. 5 is a view illustrating transmittance depending on slot shape.

Referring to FIG. 5, it shows that a frequency of terahertz electromagnetic waves exhibiting the highest transmittance differs depending on slot shape, that is, depending on whether the slot is in a rectangular shape, whether a bowtie shape is formed at the center of the rectangular shape, and the node width at the center of the bowtie shape.

Accordingly, slots may be configured to meet a natural absorption frequency of a material that is to be trapped, and thereby a particular material may be detected at low concentration with high sensitivity for terahertz electromagnetic waves.

Figure 6:
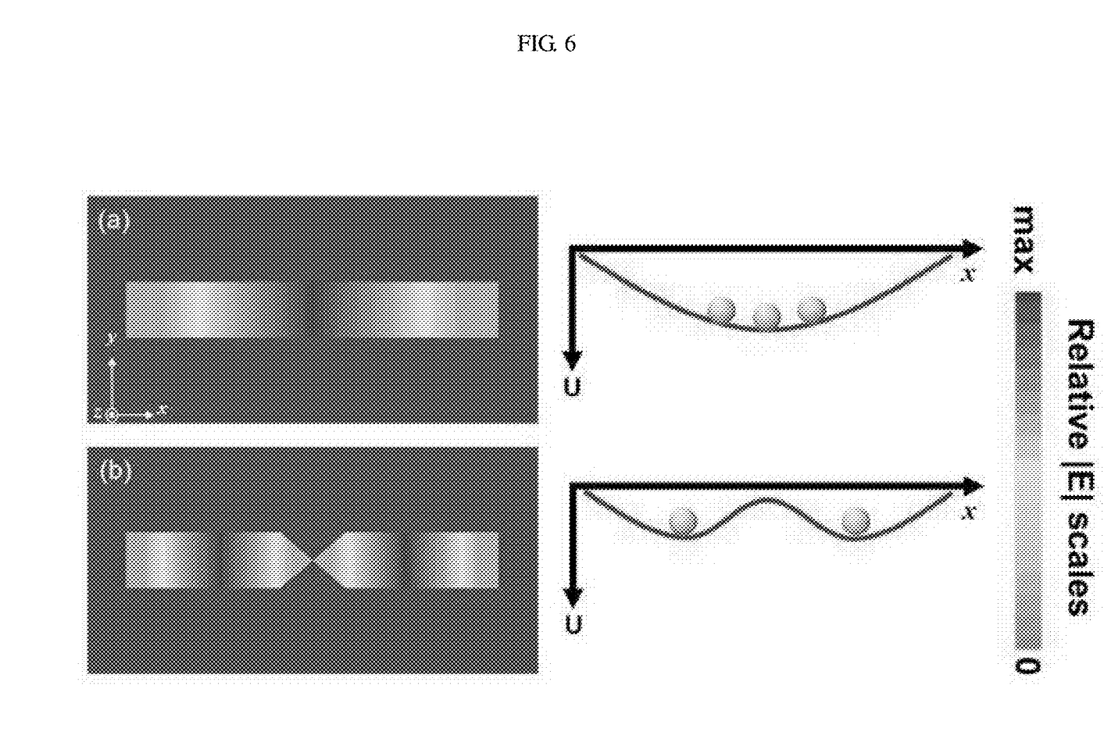
FIG. 6 is a view illustrating a distribution of terahertz electromagnetic waves and potential energy profile depending on slot shape.

FIG. 6 is a view illustrating a distribution of terahertz electromagnetic waves and potential energy profile depending on slot shape.

Referring to (a) of FIG. 6, a slot in a rectangular shape shows that particles are trapped while strong focusing of terahertz electromagnetic waves E occurs at a central portion thereof and potential energy U is minimized Referring to (b) of FIG. 6, a slot in a rectangular shape in which a bowtie shape is formed shows that a strong focusing of the terahertz electromagnetic waves does not occur at the central portion of the slot in which the bowtie shape is formed. That is, a resonance frequency changes due to the formation of the bowtie shape, and thereby strong focusing of the terahertz electromagnetic waves occurs at different portions. Here, potential energy also is minimized at the same portion at which the focusing of the electromagnetic waves occurs, and thus particles are trapped at a position different from the position at which the particles are trapped due to the slot shaped antenna.

Figure 7:
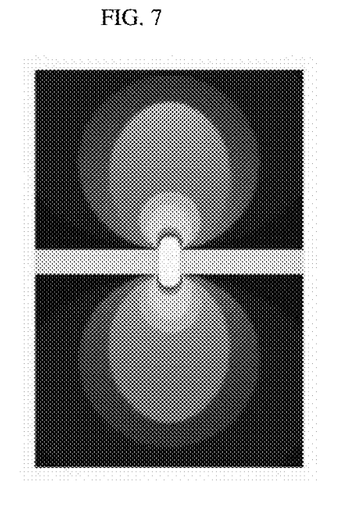
FIG. 7 is a view illustrating a distribution of terahertz electromagnetic waves at a cross-section of a slot.

FIG. 7 is a view illustrating a distribution of terahertz electromagnetic waves at a cross-section of a slot.

Referring to FIG. 7, when terahertz electromagnetic waves are incident on a slot in a rectangular shape, the terahertz electromagnetic waves incident on the slot show a distribution with gathering at the slot and then spread again like a funnel, and the terahertz electromagnetic waves focused at the cross-section of the slot become decreased in intensity with spreading away and receding from the slot. That is, strong focusing occurs while the terahertz electromagnetic waves are gathered at the slot and spread again, intensity of the focused terahertz electromagnetic waves at this point is much greater than the intensity of the incident light, and thereby particles can be trapped in a direction of the electromagnetic waves focused.

Figure 8:
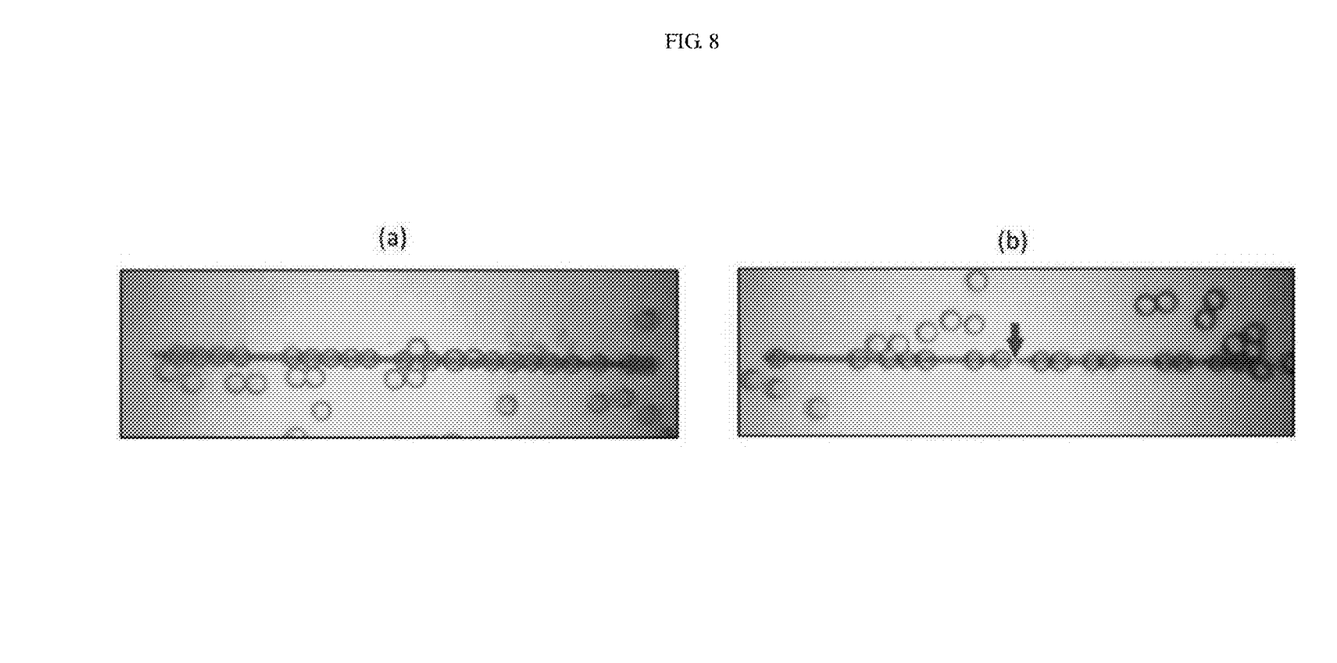
FIG. 8 is a view illustrating positions of trapped particles depending on slot shape.

FIG. 8 is a view illustrating positions of trapped particles depending on slot shape.

Referring to (a) of FIG. 8, how particles are trapped on slots is seen when a terahertz trapping device including a terahertz metamaterial having slots in a rectangular shape and a rectangular shape in which a bowtie shape is formed is irradiated with terahertz electromagnetic waves.

Referring to (a) of FIG. 8, a slot in a rectangular shape shows that particles start to become trapped from the center of the slot and positions of the particles being trapped may be determined by electric field distribution in the rectangular shape. Preferably, terahertz electromagnetic waves are increasingly focused on a slot shaped metamaterial as the width of the slot decreases, wherein particles may become trapped starting from a particular position while a distribution of a potential well due to the terahertz electromagnetic waves comes to have a form of a harmonic oscillator in a longitudinal direction of the slot. In addition, as time passes by, in the rectangular shaped slot as illustrated in (a) of FIG. 8, all particles are trapped in a longitudinal direction of the rectangular shape and this illustrates that possibility of being utilized as a sensor can be increased because particles are trapped in a wider area compared to an optical trap.

(b) of FIG. 8 is a slot in a rectangular shape in which a bowtie shape is formed and shows that positions of particles trapped are different from those in the rectangular-shaped slot according to presence of the bowtie shape. That is, in the rectangular-shaped slot in which a bowtie shape is formed, particles are trapped starting from each center of both wing portions in a rectangular shape divided based on the bowtie shape, range of sensing frequency may be broadened because resonances occurs at particular frequencies due to the bowtie shape, and thereby, a possibility of being utilized as a sensor may be increased. In addition, as time passes by, particles are trapped in a longitudinal direction in the rectangular-shaped slot in which the bowtie shape is formed as illustrated in (b) of FIG. 8, however, trapping particles is permanently impossible at the position in which the bowtie shape is formed, that is, at the position indicated by the red arrow.

Preferably, all particles are trapped in the terahertz metamaterials 110 and 210 when sufficient time passes by, and this is different from an optical trap in which particles may be trapped in a wide area and a range of the force working on gathering particles is much wider, and thereby application possibility can be increased.

Figure 9:
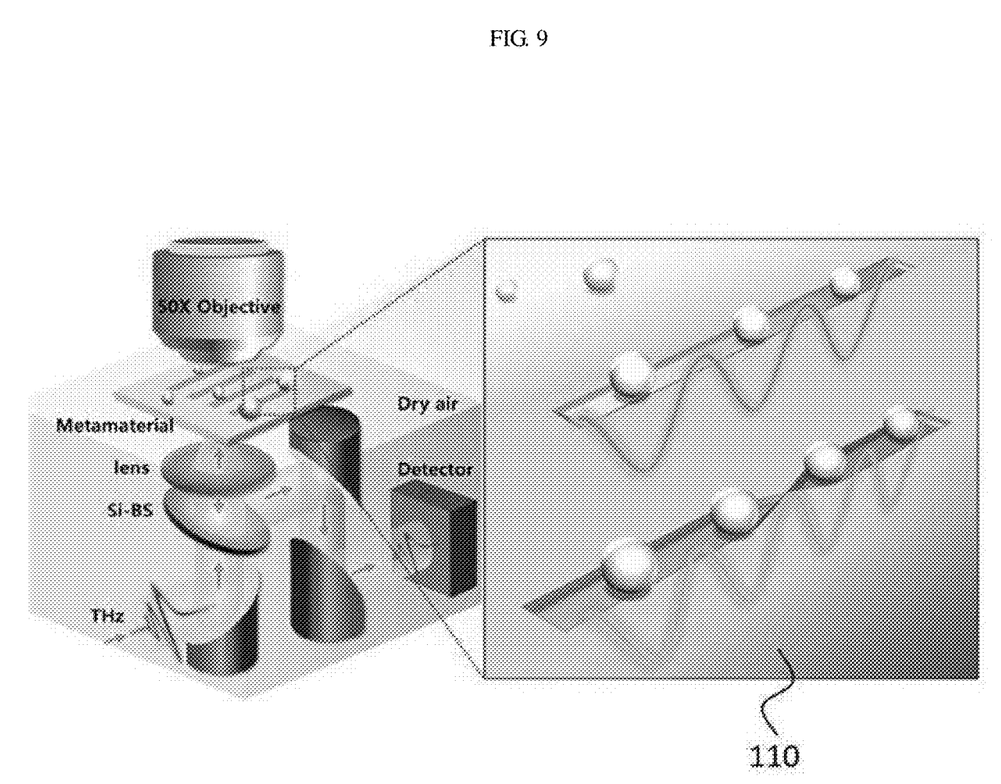
FIG. 9 is a view illustrating tweezers or a sensing system in which a terahertz metamaterial is applied according to one embodiment.

FIG. 9 is a view illustrating tweezers or a sensing system in which a terahertz metamaterial is applied according to one embodiment.

Referring to FIG. 9, the embodiments of the present invention may be used for a system which senses particles trapped in a terahertz metamaterial due to terahertz electromagnetic waves, when the terahertz metamaterial is irradiated with the terahertz electromagnetic waves, and preferably particles may be trapped at regular distances on the terahertz metamaterial 110 patterned on a metal film. That is, the terahertz metamaterial 110 may be irradiated with terahertz electromagnetic waves to enable particles to be trapped in the slots in a rectangular shape and a rectangular shape in which a bowtie shape is formed.

The terahertz trapping device to which the terahertz metamaterial is applied according to the embodiments of the present invention may be applied to a tweezers or sensing technology and may be utilized for a high-selectivity and high-sensitivity molecular sensor or for developing medical tweezers using a selective trap for a particular molecule.

That is, since molecular absorption of terahertz electromagnetic waves changes at a particular wavelength, the terahertz trapping device to which the terahertz metamaterial is applied can be utilized for a terahertz molecular sensor because selectivity between molecules is given using a fingerprinting technique, can be utilized in developing a terahertz electromagnetic wave tweezers using low-energy electromagnetic wave focusing using the terahertz metamaterial, and can be utilized in manufacturing terahertz electromagnetic waves tweezers which is selective from diverse frequencies based on manufacturing a terahertz metamaterial having a special structure.

Accordingly, the terahertz trapping devices 100 and 200 according to the embodiments of the present invention are a high-selectivity and high-sensitivity molecular sensor technology, can distinguish various bio-materials using the high-selectivity, can maximize sensing efficiency by selectively trapping for traces of a particular material, and are a non-destructive and a contactless method, thereby having an effect of being proposed as possible replacements for conventional sensing devices.

As described above, according to the embodiments of the present invention, there is an effect of enabling a non-ionized and non-destructive inspection of a bio-material.

In addition, the embodiments of the present invention can be applied to a field in which a conventional optical tweezers technology is being applied and a new field in which characteristics of the terahertz electromagnetic waves can be utilized, can particularly be applied as a technology for realizing a new molecular sensing based on the fact that diverse materials have strong absorption and spectroscopic characteristics in the terahertz frequency band, and a method of capturing micro-objects implemented by integrating a specially designed terahertz metamaterial has an effect of having diverse possible applicability for a field for which attempting a conventional optical tweezers is difficult.

In addition, the embodiments of the present invention can expand application areas in bio and medical fields in which conventional optical tweezers are used, has an effect capable of realizing ultra-high sensitivity molecular recognition sensor by trapping a molecule having a natural vibration mode when a natural vibration mode of a molecule which forms a micro-object or a natural vibration mode of a molecule that is strongly coupled to a micro-object is in the terahertz electromagnetic wave band because natural vibration (or absorption) modes of diverse molecules exist in the terahertz electromagnetic wave band, can increase spatial density of molecules to be detected by integrating with a conventional selective molecular sensing technology, and thereby having an effect of achieving sensitivity that is comparable to the level of a conventional bio sensor or mass spectrometry.

Although exemplary embodiments of the terahertz trapping device according to the present invention has been described above, the present invention is not limited thereto, and various modifications may be made within the scope of the claims, the detailed description of the embodiments, and the accompanying drawings, therefore it should be noted that such modifications belong to the scope of the claims below.

REFERENCE NUMERALS

100: TERAHERTZ TRAPPING DEVICE
110: METAMATERIAL
120: FILM
130: SUBSTRATE
200: TERAHERTZ TRAPPING DEVICE
210: METAMATERIAL

What is claimed is:

1. A terahertz trapping device, comprising:
a substrate; and
a film disposed on the substrate,
wherein the film comprises a patterned slot engraved in the film or a patterned structure embossed on the film,
wherein the terahertz trapping device is configured to control a motion of a particle using terahertz electromagnetic waves, and
wherein the patterned slot or the patterned structure is formed according to a natural absorption frequency of the particle.

2. The terahertz trapping device of claim 1, wherein the particle on the film is induced to be trapped in the patterned slot the patterned structure by the terahertz electromagnetic waves.

3. The terahertz trapping device of claim 1, wherein the terahertz electromagnetic waves are in a range of 0.1 to 2.5 THz, and are amplified and focused due to the film.

4. The terahertz trapping device of claim 1, wherein the patterned slot or the patterned structure comprises a rectangular shape, and is part of an arrangement of duplicates of the patterned slot or the patterned structure.

5. The terahertz trapping device of claim 4, wherein the patterned slot or the patterned structure comprises a bowtie shape formed at a center of the rectangular shape.

6. The terahertz trapping device of claim 4, wherein the patterned slot or the patterned structure and the duplicates of the patterned slot or the patterned structure form an array, and each of the patterned slot or the patterned structure and the duplicates of the patterned slot or the patterned structure are spaced apart from each other by a distance of 0 to 1 mm.

7. The terahertz trapping device of claim 4, wherein a length of the patterned slot or the patterned structure is 10 μm to 1 mm.

8. The terahertz trapping device of claim 1, wherein the substrate is formed of any one of quartz, silicon, sapphire, and glass which is not influenced by the terahertz electromagnetic waves.

9. The terahertz trapping device of claim 1, wherein the film is formed of any one of gold, silver, copper, and aluminum.

10. A terahertz trapping device, comprising:
a substrate; and
a film disposed on the substrate,
wherein the film comprises a patterned slot engraved in the film or a patterned structure embossed on the film,
wherein the terahertz trapping device is configured to control a motion of a particle using terahertz electromagnetic waves, and
wherein the terahertz electromagnetic waves are in a range of 0.1 to 2.5 THz, and are amplified and focused due to the film.

11. A terahertz trapping device, comprising:
a substrate; and
a film disposed on the substrate,
wherein the film comprises a patterned slot engraved in the film or a patterned structure embossed on the film,
wherein the terahertz trapping device is configured to control a motion of a particle using terahertz electromagnetic waves, and
wherein the slot or the structure comprises a rectangular shape, and is part of an arrangement of patterned slots or patterned structures.

* * * * *